United States Patent
Aoki et al.

(10) Patent No.: US 8,742,169 B2
(45) Date of Patent: Jun. 3, 2014

(54) ACROLEIN MANUFACTURING METHOD AND ACRYLIC ACID MANUFACTURING METHOD

(75) Inventors: Takanori Aoki, Tokyo (JP); Masayuki Yoshimura, Tokyo (JP)

(73) Assignee: Showa Denko K.K., Tokyo (JP)

( * ) Notice: Subject to any disclaimer, the term of this patent is extended or adjusted under 35 U.S.C. 154(b) by 356 days.

(21) Appl. No.: 12/996,335

(22) PCT Filed: Jun. 4, 2009

(86) PCT No.: PCT/JP2009/060216
§ 371 (c)(1),
(2), (4) Date: Dec. 3, 2010

(87) PCT Pub. No.: WO2009/148105
PCT Pub. Date: Dec. 10, 2009

(65) Prior Publication Data
US 2011/0087050 A1    Apr. 14, 2011

(30) Foreign Application Priority Data
Jun. 5, 2008  (JP) .................................. 2008-148095

(51) Int. Cl.
*C07C 51/16* (2006.01)
*C07C 45/00* (2006.01)

(52) U.S. Cl.
USPC ......................................... 562/532; 568/449

(58) Field of Classification Search
None
See application file for complete search history.

(56) References Cited

U.S. PATENT DOCUMENTS

| 1,916,743 | A | 7/1933 | Schwenk et al. | |
| 7,910,771 | B2 * | 3/2011 | Dubois et al. | 562/532 |
| 8,178,719 | B2 * | 5/2012 | Shima et al. | 562/535 |
| 2007/0129570 | A1 | 6/2007 | Shima et al. | |
| 2008/0183019 | A1 * | 7/2008 | Redlingshofer et al. | 568/41 |
| 2008/0214384 | A1 * | 9/2008 | Redlingshofer et al. | 502/41 |
| 2009/0134357 | A1 | 5/2009 | Bub et al. | |
| 2010/0094066 | A1 * | 4/2010 | Suppes | 568/861 |
| 2010/0113833 | A1 * | 5/2010 | Redlingshofer et al. | 568/41 |
| 2010/0168472 | A1 * | 7/2010 | Bogan et al. | 562/532 |

FOREIGN PATENT DOCUMENTS

| JP | 2005-213225 A | 8/2005 |
| JP | 2006-290815 A | 10/2006 |
| JP | 2007-301505 A | 11/2007 |
| JP | 2008-110298 A | 5/2008 |
| JP | 2008-531628 A | 8/2008 |
| WO | 2006/092272 A2 | 9/2006 |
| WO | 2007/132926 A1 | 11/2007 |

* cited by examiner

*Primary Examiner* — Karl J Puttlitz
(74) *Attorney, Agent, or Firm* — Sughrue Mion, PLLC

(57) ABSTRACT

The present invention relates to a method for producing acrolein, comprising step (1) of subjecting glycerol to dehydration reaction in the presence of a copper compound and a compound containing a heteroatom; step (2) of recovering acrolein generated in the dehydration reaction step (1); step (3) of recovering part or all of the copper compound which remained after the recovery of acrolein; step (4) of treating part or all of the recovered copper compound with at least one member selected from a group consisting of an oxidizing agent and acid; and step (5) of returning part or all of the copper compound treated in the above step to step (1); and a method for producing acrylic acid, comprising reacting acrolein obtained by the above method with molecular oxygen. The production method of the present invention enables efficient production of acrolein and acrylic acid from glycerol contained in plant oil and animal fats derived from carbon dioxide in air without depending on the oxidation of propylene derived from fossil resources.

9 Claims, No Drawings

ACROLEIN MANUFACTURING METHOD AND ACRYLIC ACID MANUFACTURING METHOD

TECHNICAL FIELD

The present invention relates to a method for producing acrolein and acrylic acid by using glycerol. Specifically, the present invention relates to a method for producing acrolein comprising a step of dehydration reaction of glycerol in the presence of a copper compound and a compound containing a heteroatom; and a method for producing acrylic acid by oxidizing the acrolein obtained by the method.

BACKGROUND ART

Generally, acrolein and acrylic acid are produced by oxidizing propylene which is a fossil resource. However, there are concerns over the increase of carbon dioxide in the air in the production method depending on fossil resources. There are also fears of depletion of fossil resources in future.

Therefore, using glycerol in the acrolein production has been studied which is generated as a by-product during the production of Bio Diesel Fuel from vegetable oil or animal fat or production of soap. That is, a method for producing acrolain by dehydrating glycerol generated as a by-product has been studied.

Here, since glycerol generated from vegetable oil has advantages that there are no fears of depletion since the glycerol is derived from plants and that the glycerol does not substantially contribute to the increase of carbon dioxide in air since the carbon source of the glycerol is carbon dioxide in the air. Animal oil and fat are the resource produced by the intake of feedstuff such as vegetable oil by livestock and it can be considered that the carbon source of the animal oil and fat is the carbon dioxide in the air.

As a method for producing acrolein by glycerol dehydration reaction, a method of using an acid catalyst has been known.

For example, U.S. Pat. No. 1,916,743 (Patent Document 1) discloses a method of reacting glycerol in a vapor phase in the presence of a catalyst supporting copper phosphate (I). However, the document does not teach reacting glycerol in the presence of a compound containing a heteroatom.

JP-A-2006-290815 (Patent Document 2) discloses a method of reacting glycerol by dissolving or dispersing glycerol in a solvent. However, the document does not teach using a copper compound as a catalyst. Besides, though the document describes using sulfolane as a solvent, it does not have a specific description such as examples.

Also, both of the above two methods have had a problem of a low yield of acrolein.

PRIOR ART

Patent Document
Patent Document 1: U.S. Pat. No. 1,916,743
Patent Document 2: JP-A-2006-290815

DISCLOSURE OF THE INVENTION

Problem to be Solved by the Invention

An object of the present invention is to provide a method for producing acrolein by dehydration reaction of glycerol in the presence of a copper compound and a compound containing a heteroatom with higher yield than in a conventional method.

Also, another object of the present invention is to provide a method for producing acrylic acid from glycerol with higher yield than in a conventional method.

Means to Solve the Problem

As a result of intensive studies to solve the above problems, the present inventors have found that acrolein can be efficiently obtained by subjecting glycerol to dehydration reaction in the presence of a copper compound and a compound containing a heteroatom. Based on this finding, the present inventors have invented the method for producing acrolein and the method for producing acrylic acid as described below.

That is, the present invention relates to a method for producing acrolein and the method for producing acrylic acid as described below.

1. A method for producing acrolein comprising a step of dehydration reaction of glycerol in the presence of a copper compound and a compound containing a heteroatom.
2. The method for producing acrolein as described in 1 above, comprising step (1) of subjecting glycerol to dehydration reaction in the presence of a copper compound and a compound containing a heteroatom; step (2) of recovering acrolein generated in the dehydration reaction step (1); step (3) of recovering part or all of the copper compound remaining after step (2); step (4) of treating part or all of the copper compound recovered in step (3) with at least one member selected from a group consisting of an oxidizing agent and acid; and step (5) of returning part or all of the copper compound treated in step (4) to step (1).
3. The method for producing acrolein as described in 2 above, wherein step (1) of dehydration reaction of glycerol and step (2) of recovering acrolein are conducted simultaneously.
4. The method for producing acrolein as described in 2 above, wherein step (1) of dehydration reaction of glycerol, step (2) of recovering acrolein and step (3) of recovering part or all of the copper compound are conducted simultaneously.
5. The method for producing acrolein as described in 1 above, wherein the copper compound is at least one member selected from a group consisting of sulfate, pyrosulfate, phosphate, pyrophosphate, nitrate, carbonate, carboxylate, halogenated compound and oxide of copper.
6. The method for producing acrolein as described in 1 above, wherein the compound containing a heteroatom is at least one member selected from a group consisting of a sulfur-containing compound, an oxygen-containing compound and a nitrogen-containing compound.
7. The method for producing acrolein as described in 6 above, wherein the compound containing a heteroatom is a sulfur-containing compound.
8. The method for producing acrolein as described in 7 above, wherein the sulfur-containing compound is at least one member selected from a group consisting of sulfone, sulfoxide, sulfide and disulfide.
9. The method for producing acrolein as described in 6 above, wherein the compound containing a heteroatom is an oxygen-containing compound.
10. The method for producing acrolein as described in 9 above, wherein the oxygen-containing compound is at least one member selected from a group consisting of ether, alcohol, carboxylic acid and ester.

11. The method for producing acrolein as described in 6 above, wherein the compound containing a heteroatom is a nitrogen-containing compound.
12. The method for producing acrolein as described in 11 above, wherein the nitrogen-containing compound is at least one member selected from a group consisting of amine, amide and nitrile.
13. The method for producing acrolein as described in 2 above, wherein the oxidizing agent is at least one member selected from a group consisting of sulfuric acid, nitric acid, oxygen, hydrogen peroxide, peroxycarboxylic acid, halogen and ozone.
14. The method for producing acrolein as described in 2 above, wherein the acid is at least one member selected from a group consisting of sulfuric acid, sulfurous acid, pyrosulfuric acid, phosphoric acid, pyrophosphoric acid, nitric acid, carboxylic acid and halogenated hydrogen.
15. A method for producing acrylic acid, comprising reacting acrolein produced by the method described in any one of 1 to 14 above with molecular oxygen.

Effects of the Invention

The method for producing acrolein of the present invention enables producing acrolein from glycerol efficiently. Also, the method for producing acrylic acid of the present invention enables producing acrylic acid from glycerol efficiently.

Mode for Carrying out the Invention

Method for Producing Acrolein

The embodiment of the method for producing acrolein of the present invention is described below.

The method for producing acrolein of the present embodiment comprises a step of obtaining acrolein by subjecting glycerol in a glycerol-containing mixture to dehydration reaction in the presence of a copper compound and a compound containing a heteroatom (referred to as "step (1)" hereinafter); a step of recovering acrolein generated in the dehydration reaction step (1) (hereinafter referred to as "step (2)"); a step of recovering part or all of the copper compound remaining after step (2) (hereinafter referred to as "step (3)"); a step of treating part or all of the copper compound recovered in step (3) with at least one member selected from a group consisting of an oxidizing agent and acid (hereinafter referred to as "step (4)"); and a step of returning part or all of the copper compound treated with acid in step (4) to step (1) (hereinafter referred to as "step (5)").

Step (1)

As a copper compound used in step (1), preferred is a compound selected from sulfate, pyrosulfate, phosphate, pyrophosphate, nitrate, carbonate, carboxylate, a halogenated compound and oxide in terms of high reaction efficiency.

The valence of the copper compound may be either monovalent or bivalent. It is also possible to use a zero-valent metal copper as a starting material after undergoing oxidation in advance or in a reaction system.

A copper compound may be used as it is or as a compound supported on a support. Examples of a support for supporting a copper compound include an oxide or composite oxide such as silica, alumina, titania, zirconia, magnesia and silica alumina; activated carbon; zeolite; aluminum phosphate; a laminated compound; and silicon carbide.

Examples of a method for supporting a copper compound include an impregnation method, a coprecipitation method, a deposition method, a kneading method, an ion exchange method and a fusion method.

A copper compound may also be sintered in a gas in suit with the intended use. Examples of the gas include nitrogen, argon, helium and air.

There is no particular limitation on the shape of a copper compound. Examples of the shape include powder, a spherical form, a cylindrical form, a saddle shape and a honeycomb type.

Examples of the glycerol as a raw material include those commercially or industrially available such as purified glycerol and crude glycerol. As crude glycerol, crude glycerol generated as a by-product during the production of Bio Diesel Fuel and soap may be used. Also, glycerol may contain one or more compound selected from a group consisting of aliphatic acid, fatty acid salt, glyceride, aliphatic acid ester, an alkaline compound, an alkali salt compound, alcohol and water. Or glycerol may be diluted with a solvent which does not affect the reaction. Specific examples of a solvent which does not affect the reaction include liquid paraffin; paraffin wax; saturated hydrocarbon such as dodecane, tridecane, tetradecane and hexadecane; aromatic hydrocarbon such as dibenzyl; and silicone oil.

The hydration reaction in the present invention is performed in the presence of a compound containing a heteroatom. It is preferable to use the compound containing a heteroatom which doubles as a solvent in a liquid-phase reaction because the reaction efficiency is improved by the use.

Examples of a compound containing a heteroatom include a sulfur-containing compound, an oxygen-containing compound and a nitrogen-containing compound. The compound containing a heteroatom in the present invention means an organic compound containing an element such as sulfur, oxygen and nitrogen which is other than carbon and hydrogen.

As an oxygen-containing compound, at least one oxygen-containing compound selected from ether, alcohol, carboxylic acid and ester is preferred.

As ether, preferred examples include diethyl ether, dipropyl ether, dibutyl ether, dipentyl ether, diphenyl ether, anisole, furan, tetrahydrofuran, pyran, tetrahydropyran, dioxolan, dioxane, dimethoxymethane, ethylene glycol dimethyl ether, ethylene glycol diethyl ether, diethylene glyocol dimethyl ether and diethylene glycol diethyl ether.

As alcohol, preferred are methanol, ethanol, propanol, butanol, pentanol, cyclopentanol, hexanol, cyclohexanol, heptanol, furfuryl alcohol, phenol, catechol, resorcinol, hydroquinone, benzyl alcohol, diphenyl carbinol, triphenyl carbinol, ethylene glycol, propylene glycol and pentaerythritol.

Examples of carboxylic acid include acetic acid, propionic acid, butanoic acid, valeric acid, caproic acid, caprylic acid, capric acid, lauric acid, myristic acid, palmitic acid, stearic acid, arachic acid, behenic acid, lignoceric acid, oleic acid, cetoleic acid, erucic acid, brassidic acid, sorbic acid, linoleic acid, linolenic acid, arachidonic acid, eicosenoic acid, ricinolic acid, cyclohexanecarboxylic acid, phenylacetic acid, benzoic acid, hydroxybenzoic acid, malonic acid, succinic acid, glutaric acid, adipic acid, phthalic acid, isophthalic acid, terephthalic acid and salicylic acid.

Examples of ester include methyl acetate, ethyl acetate, propyl acetate, butyl acetate, pentyl acetate, hexyl acetate, methyl propionate, ethyl propionate, propyl propionate, butyl propionate, pentyl propionate, hexyl propionate, methyl butanoate, ethyl butanoate, propyl butanoate, butyl butanoate, pentyl butanoate, hexyl butanoate, methyl adipate, ethyl adipate, propyl adipate, butyl adipate, pentyl adipate, hexyl adipate, methyl benzoate, ethyl benzoate, propyl benzoate, butyl benzoate, pentyl benzoate, hexyl benzoate, dimethyl phthalate, dimethyl isophthalae, dimethyl terephthalate, butyrolactone and valerolactone.

As a nitrogen-containing compound, preferred is at least one member selected from amine, amide and nitrile.

Examples of amine include trimethylamine, triethylamine, tripropylamine, tributylamine, tripentylamine, trihexylamine, tricyclohexylamine, diphenylamine, triphenylamine, aniline, N-methylaniline, N,N-dimethylaniline, toluidine, anisidine, ethylenediamine, tetramethylenediamine, hexamethylenediamine, diethylenetriamine, triethylenetetramine, pyrrole, pyrolidine, pyridine, piperidine, phenanthroline and bipyridyl.

Examples of amide include formamide, acetamide, propionamide, hexanamide, benzamide, acetanilide, benzanilide, acetotoluidide and phthalimide.

Examples of nitrile include acetonitrile, propionitrile, butyronitrile, valeronitrile, adiponitrile, benzonitrile and tolunitrile.

As a sulfur-containing compound, preferred is at least one member of sulfur-containing compounds selected from the group consisting of sulfone, sulfoxide, sulfide and disulfide.

As sulfone, preferred is one member selected from dimethyl sulfone, methyl ethyl sulfone, methyl propyl sulfone, methyl butyl sulfone, methyl phenyl sulfone, diethyl sulfone, ethyl propyl sulfone, ethyl butyl sulfone, ethyl phenyl sulfone, dipropyl sulfone, propyl butyl sulfone, propyl phenyl sulfone, dibutyl sulfone, butyl phenyl sulfone, diphenyl sulfone, sulfonal, trional, tetronal, sulfolane, methyl sulfolane, dimethyl sulfolane, ethyl sulfolane, diethyl sulfolane, propyl sulfolane, dipropyl sulfolane, butyl sulfolane and dibutyl sulfolane.

As sulfoxide, preferred are dimethyl sulfoxide, methyl ethyl sulfoxide, methyl propyl sulfoxide, methyl butyl sulfoxide, methyl phenyl sulfoxide, diethyl sulfoxide, ethyl propyl sulfoxide, ethyl butyl sulfoxide, ethyl phenyl sulfoxide, dipropyl sulfoxide, propyl butyl sulfoxide, propyl phenyl sulfoxide, dibutyl sulfoxide, butyl phenyl sulfoxide, diphenyl sulfoxide, tetra methylene sulfoxide and the like. More preferred are dimethyl sulfoxide, diethyl sulfoxide, dipropyl sulfoxide, dibutyl sulfoxide, diphenyl sulfoxide, tetramethylene sulfoxide and the like.

As sulfide, preferred are dimethyl sulfide, methyl ethyl sulfide, methyl butyl sulfide, diethyl sulfide, ethyl propyl sulfide, ethyl butyl sulfide, ethyl phenyl sulfide, dipropyl sulfide, dibutyl sulfide, diphenyl sulfide, thiophene, tetramethylene sulfide and the like. More preferred are dimethyl sulfide, diethyl sulfide, dipropyl sulfide, dibutyl sulfide, thiophene, diphenyl sulfide, tetramethylene sulfide and the like.

As disulfide, preferred are dimethyl disulfide, diethyl disulfide, dipropyl disulfide, dibutyl disulfide, diphenyl disulfide and the like. More preferred are dibutyl disulfide, diphenyl disulfide and the like.

A method of dehydration reaction may either a liquid-phase reaction or a gas-phase reaction. The reaction mode may either be a batch mode, a semi-batch mode or a continuous mode.

The dehydration reaction can be conducted at a temperature from 0 to 500° C. The temperature is preferably from 100 to 500° C., and more preferably from 150 to 400° C., which provides high reaction efficiency.

Since an increase in the mole number accompanies the dehydration reaction of glycerol, the lower the reaction pressure is, the higher the acrolein yield becomes. Specifically, the pressure is preferably from 0.01 to 10.0 MPa, and more preferably from 0.05 to 5 MPa.

In the case of a liquid-phase reaction, a temperature and a pressure which allow glycerol and a compound containing a heteroatom to exist in a liquid state should be selected. Meanwhile in the case of a gas-phase reaction, a temperature and a pressure which allow glycerol and a compound containing a heteroatom to exist in a gas state should be selected.

In the case of a gas-phase reaction, glycerol and a compound containing a heteroatom may be diluted with inert gas. As inert gas, nitrogen, carbon dioxide, rare gas such as helium and argon, steam and the like may be used.

The acrolein content in the acrolein-containing mixture obtained in step (1) is determined by the glycerol content in the glycerol-containing mixture, the yield of the dehydration reaction and the like. However, the content is preferably from 5 to 60 mass % specifically.

Step (2)

As a method for recovering acrolein generated by dehydration reaction, any known recovering method may be employed. However, to recover acrolein industrially, a distillation method is preferable.

Specific examples of a distillation method include single-stage distillation, multi-stage distillation, steam distillation and flash distillation. The distillation method may either be a batch method, a semi-batch method or a continuous method.

When multi-stage distillation is employed, it is possible to distil a component having a boiling point lower than that of acrolein from the top of the distillation column, acrolein from the middle of the column and a copper compound from the bottom of the column.

In multi-stage distillation, a known distillation column such as a tray-type distillation column and a packed bed distillation column can be used.

Examples of the structure of a tray-type distillation column include a bubble tray, a sieve tray, a valve tray, a super-flux tray and a max-flux tray.

Examples of the packing material for the packed distillation column include structured packing and random packing. Examples of structured packing include a metal-plate type, a metal-wire type and a grid type. Examples of random packing include a Raschig ring, a Lessing ring, a Berl saddle, an Intalox saddle, a Tellerette, a Pall ring, a flexi-ring and a cascade ring.

As the distillation conditions, the temperature of the column bottom can be adjusted to from 0 to 500° C., preferably from 0 to 100° C., more preferably from 5 to 80° C., and still more preferably from 10 to 60° C. When the temperature of the column bottom is higher than 500° C., acrolein may polymerize in some cases. When the temperature of the column bottom is lower than 0° C., the energy required for cooling tends to increase. The distillation pressure is determined depending on the relationship with the temperature.

When distilling a reaction product containing acrolein, it is desirable to add a polymerization inhibitor in advance to prevent the polymerization of acrolein. Examples of the polymerization inhibitor include phenothiazine and a phenol compound such as phenol, hydroquinone, methoquinone, catechol and cresol. When a polymerization inhibitor is added, the added amount of the polymerization inhibitor is preferably from 1 mass ppm to 1 mass % to 100 mass % of acrolein.

Step (2) may be performed after step (1) or simultaneously with step (1).

As a specific embodiment of performing step (2) simultaneously with step (1), for example, a glycerol-containing mixture as a raw material may be supplied to a reactor provided with a distillation column for a liquie-phase reaction; and concurrently with the production of acrolein by dehydration reaction, the generated acrolein may be recovered from the top or side of the distillation column.

When step (2) is performed simultaneously with step (1), the temperature of the column bottom may be adjusted to the reaction temperature in step (1). For example, the temperature of the column bottom is preferably from 100 to 500° C., and more preferably 150 to 400° C. in view of maintaining high reaction efficiency. The distillation pressure is determined depending on the relationship with the temperature.

In step (2), a compound containing a heteroatom can be recovered concurrently with recovering acrolein. The recovered compound containing a heteroatom can be returned to step (1) for reuse.

The acrolein obtained in step (2) may be used as a material of acrylic acid, methionine, 1,3-propanediol, ally alcohol and the like.

Step (3)

As a method for recovering part or all of the copper compound remaining after step (2), any known method can be employed. When the copper compound is precipitated as a solid, a known method such as filtration, expression, centrifugation, sedimentation and flotation separation may be used. For example, the separation by filtration may be performed either by natural filtration, pressure filtration or filtration under reduced pressure; the separation by sedimentation may be performed either by clarification separation or concentration sedimentation; and the flotation separation may be performed either by pressure flotation or electrolytic flotation.

To recover a copper compound when it is dissolved in liquid, any known method can be employed. Examples of the method include a method of recovering the liquid after a solid is separated and removing a solvent by distillation and the like.

In step (3), a compound containing a heteroatom can be recovered concurrently with recovering a copper compound. The recovered compound containing a heteroatom can be returned to step (1) for reuse.

Step (4)

As a method of treating part or all of the copper compound recovered in step (3) with at least one member selected from an oxidizing agent and acid, any known method can be employed.

A copper compound may be reduced to metal copper along with the progress of dehydration reaction in some cases, it is desirable to treat the copper compound with an oxidizing agent.

Examples of the oxidizing agent include an oxidizing agent which is at least one member selected from a group preferably consisting of sulfuric acid, nitric acid, oxygen, hydrogen peroxide, percarboxylic acid, halogen and ozone. Two or more of oxidizing agents may be used in combination and, for example, a mixed acid of such as sulfuric acid and nitric acid can be used.

Examples of sulfuric acid include a compound comprising sulfuric acid such as dilute sulfuric acid, concentrated sulfuric acid, hot concentrated sulfuric acid and fuming sulfuric acid.

As an oxygen source, oxygen and a gas obtained by diluting oxygen with inert gas can be used. For example, air may be used.

Examples of percaboxylic acid include peracetic acid, perpropionic acid and perbenzoic acid.

Examples of halogen include fluorine, chlorine, bromine and iodine.

As acid, preferred is at least one member selected from a group preferably consisting of sulfuric acid, sulfurous acid, pyrosulfuric acid, phosphoric acid, pyrophosphoric acid, nitric acid, carboxylic acid and halogenated hydrogen.

In the case where acid is used, it is preferable to use acid having the same anion as that of the copper compound used in dehydration reaction.

Examples of halogenated hydrogen include hydrogen fluoride, hydrogen chloride, hydrogen bromide and hydrogen iodide.

Also, two or more kinds of acids may be used in combination.

An oxidizing agent and acid may be used at the same time. Also, a compound having properties of both an oxidizing agent and acid may be used. Examples of such a compound include sulfuric acid.

It is possible to recover an oxidizing agent and acid attached to or taken in a copper compound by washing the copper compound treated in a process of treating the copper compound with at least one member selected from a group consisting of an oxidizing agent and acid with a solvent. As a solvent for washing, the same solvent as the one used in the reaction or another solvent may be used. Also, the mixture of the solvents may be used.

In the case where a copper compound is dissolved when part or all of the copper compound is treated with at least one member selected from a group consisting of an oxidizing agent and acid, the copper compound can be precipitated as a solid by the addition of a solvent. As a solvent to be added, the same solvent as the one used in the reaction or another solvent may be used. Also, the mixture of the solvents may be used.

Step (5)

As a method of returning part or all of the copper compound treated with at least one member selected from an oxidizing agent and acid in step (4), any known method may be employed. On this occasion, a copper compound may be newly added.

[Method for Producing Acrylic Acid]

Next, an embodiment of the method for producing acrylic acid of the present invention is to be described below.

The method of producing acrylic acid of the present invention is a method of obtaining acrylic acid by oxidizing acrolein obtained in the above-mentioned method of producing acrolein with molecular oxygen.

The above oxidation reaction preferably uses an oxidation reaction catalyst in order to increase the reaction speed. Examples of the oxidation reaction catalyst include a solid catalyst including a metal oxide, and a mixture and a composite oxide thereof. Examples of the metal constituting the metal oxide include one or more member selected from a group consisting of iron, molybdenum, titanium, vanadium tungsten, antimony, tin and copper.

The oxidation catalyst may be a support catalyst configured to support the oxide above on a support. Examples of the support include silica, alumina, zirconia, and a mixture or oxide composite thereof and silicon carbide.

There is no particular limitation on the form of the catalyst and it includes a particulate form, a spherical form, a cylindrical form, a saddle-shaped form and a honey-comb form.

Examples of the method of preparing the catalyst include an impregnation method, a precipitation method and an ion exchange method.

The catalyst may be fired in a gas in advance. Examples of the gas include nitrogen, argon, helium and air.

The oxidation reaction may be conducted either in a liquid phase reaction using a fixed bed or a gaseous phase reaction using a fluid bed.

The temperature of the oxidation reaction is preferably 150 to 400° C., and more preferably 200 to 350° C. in view of increasing reaction efficiency.

The pressure of the oxidation reaction is preferably 0.01 to 10 MPa, and more preferably 0.05 to 10 MPa.

The molecular oxygen in the oxidation reaction may be supplied in the form of oxygen gas or may be supplied as air.

An inert gas may be added in the oxidation reaction. Examples of the inert gas include nitrogen, carbon dioxide, a rare gas such as helium and argon, and steam.

The gas composition during the oxidation reaction must be adjusted to avoid an explosive range. Examples of such a composition include a composition of 1-15 volume % of acrolein, 0.5-25 volume % of oxygen, 0-50 volume % of water vapor and 20-80 volume % of nitrogen.

Generally, acrolein obtained in step (2) is used in the oxidation reaction. However, the gaseous acrolein as it is obtained in step (1) may be provided to the reaction after being mixed with molecular oxygen and inert gas such as water vapor. In this case, two connected reaction vessels or a single reaction vessel may be used which is used in the production of acrylic acid from propylene by two-stage vapor-phase oxidation and the like.

In order to prevent polymerization of the acrylic acid obtained by the oxidation reaction, it is preferable to add a polymerization inhibitor. The same polymerization inhibitor as the one to be added to acrolein may be used. The added amount of the polymerization inhibitor in the case where a polymerization inhibitor is added is preferably 1 mass ppm to 1 mass % to 100 mass % of acrylic acid.

It is preferable to purify the acrylic acid obtained by the oxidation reaction in order for use in various chemical products and materials of a polymer. The purification methods are the same as those for purifying acrolein, and preferred is a distillation method. A distillation method similar to the one used for the distillation of acrolein may be employed.

As the distillation conditions when the acrylic acid is subjected to multi-stage distillation, the temperature of the column bottom is preferably from 0 to 120° C., more preferably from 5 to 100° C., and still more preferably from 10 to 80° C. When the temperature of the column bottom is higher than 120° C., acrylic acid may polymerize in some cases. When the temperature of the column bottom is lower than 0° C., the energy required for cooling tends to increase. The distillation pressure is determined depending on the relationship with the temperature.

Similar to the method for producing acrolein, the above-described method for producing acrylic acid enables efficient production of acrylic acid from a mixture containing glycerol with less energy consumption.

EXAMPLES

The invention will be described with reference to Examples below, but the invention is not limited thereto.

Example 1

In a 500 ml-volume four-necked flask provided with a single distillation tube, a thermometer and a stirrer, 9.2 g of Copper(II)sulfate pentahydrate as a catalyst and 150 g of sulfolane as a solvent were charged and vigorously stirred under a nitrogen atmosphere, dipped in an oil bath and heated to 280° C. After the temperature is stabilized, a glycerol mixture comprising 90 mass % of glycerol and 10 mass % of water was supplied to the flask at a rate of 33.3 g/hour (h) to perform reaction. After supplying the glycerol mixture for one hour, the mixture was reacted for another hour. The gas and liquid distilled from the single distillation tube were cooled to be condensed. The distillate and residual liquid remained at the bottom of the flask after the reaction were analyzed by gas chromatography. The glycerol conversion was 100% and the acrolein yield in terms of glycerol was 80%. The glycerol conversion and acrolein yield were determined by means of the following formulae.

Glycerol conversion(%)={(mole number of supplied glycerol)−(the mole number of unreacted glycerol)/(mole number of supplied glycerol)}×100  [Formula 1]

Acrolein yield(%)={(mole number of generated acrolein)/(mole number of supplied glycerol)}×100  [Formula 2]

Example 2

The reaction was conducted in the same way as in Example 1 except that the glycerol mixture was supplied for three hours instead of one hour. The glycerol conversion was 97% and the acrolein yield against the glycerol standard was 60%.

Example 3

The reaction was conducted in the same way as in Example 2 except that Copper(II)sulfate pentahydrate was used in an amount of 27.5 g instead of 9.2 g. The glycerol conversion was 100% and the acrolein yield on the basis of glycerol was 72%.

Example 4

The reaction was conducted in the same way as in Example 3 except that 100 mass % of glycerol was supplied at a rate of 30 g/h for three hours instead of the glycerol mixture comprising 90 mass % of glycerol and 10 mass % of water at a rate of 33.3 g/h. The glycerol conversion was 100% and the acrolein yield on the basis of glycerol was 63%.

Example 5

The reaction was conducted in the same way as in Example 3 except that a glycerol mixture comprising 95 mass % of glycerol and 5 mass % of water was supplied at a rate of 32 g/h for three hours instead of the glycerol mixture comprising 90 mass % of glycerol and 10 mass % of water at a rate of 33.3 g/h. The glycerol conversion was 100% and the acrolein yield on the basis of glycerol was 73%.

Example 6

The reaction was conducted in the same way as in Example 2 except that Copper(II)sulfate pentahydrate was used in an amount of 50 g instead of 9.2 g and sulfolane was used in an amount of 200 g instead of 150 g. The glycerol conversion was 100% and the acrolein yield on the basis of glycerol was 75%.

Example 7

The reaction was conducted in the same way as in Example 1 except for using diphenyl sulfone instead of sulfolane.
The glycerol conversion was 100% and the acrolein yield on the basis of glycerol was 78%.

Example 8

The reaction was conducted in the same way as in Example 1 except for using diphenyl sulfoxide instead of sulfolane.

The glycerol conversion was 99% and the acrolein yield on the basis of glycerol was 78%.

Example 9

The reaction was conducted in the same way as in Example 1 except for using diphenyl sulfide instead of sulfolane.

The glycerol conversion was 98% and the acrolein yield on the basis of glycerol was 74%.

Example 10

The reaction was conducted in the same way as in Example 1 except for using diphenyl disulfide instead of sulfolane.

The glycerol conversion was 98% and the acrolein yield on the basis of glycerol was 75%.

Example 11

The reaction was conducted in the same way as in Example 1 except for using diphenyl ether instead of sulfolane.

The glycerol conversion was 93% and the acrolein yield on the basis of glycerol was 75%.

Example 12

The reaction was conducted in the same way as in Example 1 except for using diphenyl carbinol instead of sulfolane.

The glycerol conversion was 99% and the acrolein yield on the basis of glycerol was 77%.

Example 13

The reaction was conducted in the same way as in Example 1 except for using stearic acid instead of sulfolane.

The glycerol conversion was 100% and the acrolein yield on the basis of glycerol was 79%.

Example 14

The reaction was conducted in the same way as in Example 1 except for using dimethyl phthalate instead of sulfolane.

The glycerol conversion was 99% and the acrolein yield on the basis of glycerol was 79%.

Example 15

The reaction was conducted in the same way as in Example 1 except for using triphenyl amine instead of sulfolane.

The glycerol conversion was 95% and the acrolein yield on the basis of glycerol was 61%.

Example 16

The reaction was conducted in the same way as in Example 1 except for using benzanilide instead of sulfolane.

The glycerol conversion was 97% and the acrolein yield on the basis of glycerol was 72%.

Example 17

The reaction was conducted in the same way as in Example 1 except for using adiponitrile instead of sulfolane.

The glycerol conversion was 99% and the acrolein yield on the basis of glycerol was 77%.

Comparative Example 1

The reaction was conducted in the same way as in Example 1 except for using liquid paraffin instead of sulfolane as a solvent and 5 g of potassium hydrogensulfate instead of copper(II)sulfate pentahydrate.

The glycerol conversion was 97% and the acrolein yield on the basis of glycerol was 54%.

Comparative Example 2

The reaction was conducted in the same way as in Example 2 except for using liquid paraffin instead of sulfolane as a solvent and setting the oil bath temperature to 300° C.

The glycerol conversion was 92% and the acrolein yield on the basis of glycerol was 36%.

Comparative Example 3

The reaction was conducted in the same way as in Example 2 except for using 5.0 g of potassium hydrogensulfate instead of copper(II)sulfate pentahydrate.

The glycerol conversion was 83% and the acrolein yield on the basis of glycerol was 14%.

Example 18

Gas-Phase Reaction of Acrylic Acid 7.0 g of ammonium paramolybdate, 2.1 g of ammonium metavanadate, 0.89 g of ammonium paratungstate and 50 ml of water were charged in a flask and dissolved by heating to 90° C. while being stirred. A solution of copper sulfate prepared in advance by dissolving 1.8 g of copper(II)sulfate in 15 ml of water was added to the thus-obtained solution to thereby obtain a solution for preparing a catalyst.

20 g of α-alumina was impregnated with the solution for preparing a catalyst and then evaporated to dryness. After drying, α-alumina was sintered at 400° C. under air atmosphere for three hours to obtain a catalyst for oxidation reaction comprising an molybdenum-vanadium-tungsten-copper oxide supported on α-alumina.

A stainless-steel reaction tube having an inner diameter of 10 mm and a length of 300 mm was filled with 5 ml of the above catalyst for oxidation reaction. A mixed gas containing 3 volume % of acrolein obtained in Example 1, 3 volume % of oxygen, 30 volume % of water vapor and 64 volume % of nitrogen was introduced into the reaction tube at a space velocity of 3000/hour. The reaction tube was heated to 280° C. in an electric furnace, thereby subjecting the mixed gas to oxidation reaction. The outlet of the reaction tube was cooled and the resulting reaction gas was condensed and collected. Gas chromatograph analysis of the collected liquid showed that the acrolein conversion was 98% and the acrylic acid yield on the basis of acrolein was 90%.

INDUSTRIAL APPLICABILITY

The present invention enables efficient production of acrolein and acrylic acid from glycerol derived from plant oil, the carbon source of which is carbon dioxide in air, and glycerol derived from animal fats obtained from cattle feeding on plant oils and the like without depending on propylene derived from fossil resources.

The invention claimed is:

1. A method for producing acrolein, comprising step (1) of subjecting glycerol to dehydration reaction of glycerol in the presence of a copper compound and a compound containing a heteroatom; step (2) of recovering acrolein generated in the dehydration reaction step (1); step (3) of recovering part or all of the copper compound remaining after step (2); step (4) of treating part or all of the copper compound recovered in step (3) with at least one member selected from a group consisting of an oxidizing agent and acid; and step (5) of returning part or all of the copper compound treated in step (4) to step (1),
   wherein the compound containing a heteroatom is at least one member selected from the group consisting of a sulfur-containing compound, an oxygen-containing compound and a nitrogen-containing compound,
   wherein the sulfur-containing compound is at least one member selected from the group consisting of sulfone, sulfoxide, sulfide and disulfide,
   wherein the oxygen-containing compound is at least one member selected from the group consisting of ether, carboxylic acid and ester,
   wherein the nitrogen-containing compound is at least one member selected from the group consisting of amine, amide and nitrile, and
   wherein the copper compound is at least one member selected from the group consisting of sulfate, pyrosulfate, phosphate, pyrophosphate, nitrate, carbonate, carboxylate, halogenated compound and oxide of copper.

2. The method for producing acrolein as claimed in claim 1, wherein step (1) of dehydration reaction of glycerol and step (2) of recovering acrolein are conducted simultaneously.

3. The method for producing acrolein as claimed in claim 1, wherein step (1) of dehydration reaction of glycerol, step (2) of recovering acrolein and step (3) of recovering part or all of the copper compound are conducted simultaneously.

4. The method for producing acrolein as claimed in claim 1, wherein the compound containing a heteroatom is a sulfur-containing compound.

5. The method for producing acrolein as claimed in claim 1, wherein the compound containing a heteroatom is an oxygen-containing compound.

6. The method for producing acrolein as claimed in claim 1, wherein the compound containing a heteroatom is a nitrogen-containing compound.

7. The method for producing acrolein as claimed in claim 1, wherein the oxidizing agent is at least one member selected from the group consisting of sulfuric acid, nitric acid, oxygen, hydrogen peroxide, peroxycarboxylic acid, halogen and ozone.

8. The method for producing acrolein as claimed in claim 1, wherein the acid is at least one member selected from the group consisting of sulfuric acid, sulfurous acid, pyrosulfuric acid, phosphoric acid, pyrophosphoric acid, nitric acid, carboxylic acid and halogenated hydrogen.

9. A method for producing acrylic acid, comprising reacting acrolein produced by the method claimed in claim 1 with molecular oxygen.

* * * * *